United States Patent [19]

Sanderson et al.

[11] Patent Number: 5,741,952
[45] Date of Patent: Apr. 21, 1998

[54] CATALYTIC DECOMPOSITION OF PEROXIDES TO PURIFY A METHYL TERTIARY BUTYL ETHER RECYCLE STREAM

[75] Inventors: John Ronald Sanderson, Leander; John Frederick Knifton, Austin, both of Tex.

[73] Assignee: Huntsman Specialty Chemicals Corporation, Austin, Tex.

[21] Appl. No.: 2,563

[22] Filed: Jan. 11, 1993

Related U.S. Application Data

[63] Continuation-in-part of Ser. No. 833,200, Feb. 10, 1992, abandoned.
[51] Int. Cl.[6] ........................................ C07C 29/88
[52] U.S. Cl. ..................... 568/699; 568/698; 568/913; 568/914
[58] Field of Search ............................... 568/698, 699, 568/913, 914

[56] References Cited

U.S. PATENT DOCUMENTS 4,704,482   11/1987   Sanderson et al. ............... 568/922

*Primary Examiner*—Rebecca Cook
*Attorney, Agent, or Firm*—Russell R. Stolle; Ron D. Brown; Carl G. Ries

[57] ABSTRACT

An MTBE recycle stream (which consists mainly of TBA and methanol) contaminated with residual amounts of tertiary butyl hydroperoxide, ditertiary butyl peroxide and allyl tertiary butyl peroxide can be effectively catalytically treated under mild conversion conditions with a silica-supported nickel, copper, chromium, iron catalyst in order to substantially completely decompose the peroxide contaminants and to thereby provide a treated MTBE recycle stream which is not only substantially free from contaminating quantities of such peroxides, but which also contains an enhanced amount of methyl tertiary butyl ether.

2 Claims, No Drawings

CATALYTIC DECOMPOSITION OF PEROXIDES TO PURIFY A METHYL TERTIARY BUTYL ETHER RECYCLE STREAM

BACKGROUND OF THE INVENTION

This application is a continuation-in-part of copending Sanderson et al. patent application Ser. No. 07/833,200, filed Feb. 10, 1992 and entitled: "REMOVAL OF PEROXIDES FROM A METHYL TERTIARY BUTYL ETHER RECYCLE STREAM" (D#81,063) now abandoned.

FIELD OF THE INVENTION

This invention relates to the catalytic enrichment and purification of a methyl tertiary butyl ether (MTBE) recycle stream consisting essentially of tertiary butyl alcohol (TBA) and methanol (MeOH) and contaminated with minor quantities of peroxide contaminants such as tertiary butyl hydroperoxide, ditertiary butyl peroxide and allyl tertiary butyl peroxide. More particularly, this invention relates to a method for the catalytic enrichment and purification of a methyl tertiary butyl ether (MTBE) recycle stream consisting essentially of tertiary butyl alcohol (TBA) and methanol (MeOH) by the decomposition of the peroxide contaminants and by the simultaneous enrichment of the recycle stream by the conversion of peroxide contaminants to methyl tertiary butyl ether. In accordance with the present invention, a methyl tertiary butyl ether recycle stream consisting essentially of tertiary butyl alcohol and methanol and contaminated with minor quantities of peroxide contaminants such as tertiary butyl hydroperoxide, ditertiary butyl peroxide and allyl tertiary butyl peroxide is purified and enriched by bringing it into contact with a silica-supported catalyst consisting of nickel, copper, iron and chromium, as hereinafter defined, in order to decompose the peroxide contaminants and in order to substantially simultaneously convert the peroxide contaminants and methanol into methyl tertiary butyl ether.

PRIOR ART

It is known to those skilled in the art that ethers, including unsymmetrical ethers, may be prepared by reacting an alcohol with another alcohol to form the desired product. The reaction mixture, containing catalyst and/or condensing agent may be separated and further treated to permit attainment of the desired product. Such further treatment commonly includes one or more distillation operations.

Methyl tert-butyl ether (MTBE) is finding increasing use as a blending component in high octane gasoline as the current gasoline additives based on lead and manganese are phased out. Currently commercial processes for the manufacture of methyl tert-butyl ether are based upon the liquid-phase reaction of isobutylene and methanol (Eq. 1), catalyzed by a cationic ion-exchange resin (see, for example: Hydrocarbon Processing, Oct. 1984, p. 63; Oil and Gas J., Jan. 1, 1979, p. 76; Chem. Economics Handbook-SRI, Sep. 1986, p. 543-7051P). The cationic ion-exchange resins used in MTBE synthesis normally have the sulphonic acid functionality (see: J. Tejero, J. Mol. Catal., 42 (1987) 257; C. Subramamam et al., Can. J. Chem. Eng., 65 (1987) 613).

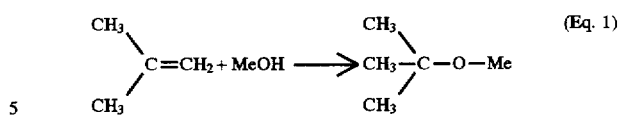
(Eq. 1)

With the expanding use of MTBE as an acceptable gasoline additive, a growing problem is the availability of raw materials. Historically, the critical raw material is isobutylene (Oil and Gas J., Jun. 8, 1987, p. 55). It would be advantageous, therefore, to have a process to make MTBE that does not require isobutylene as a building block. It would be advantageous to have an efficient process for making MTBE by reaction of methanol with tertiary butyl alcohol, since t-butanol (TBA) is readily available commercially through isobutane oxidation. However, as hereafter more fully explained, when tertiary butyl alcohol is prepared by first oxidizing isobutane to form tertiary butyl hydroperoxide and by then thermally or catalytically converting the tertiary butyl hydroperoxide to tertiary butyl alcohol, a number of oxygenation by-products are formed, including ditertiary butyl peroxide (DTBP) and allyl tertiary butyl peroxide. The oxygenation by-products adversely affect the quality of the tertiary butyl alcohol and methyl tertiary butyl ether made therefrom and are removed only with difficulty.

There is a substantial body of prior art directed to the purification of methyl tertiary butyl ether prepared from isobutylene and methanol. In this situation, the oxygenation by-products are not present in either of the feed materials or in the methyl tertiary butyl ether product.

In U.S. Pat. No. 4,144,138 (1979) to Rao et al., there is disclosed a method for recovering methyl tertiary butyl ether from etherification reaction effluent by azeotropic distillation to recover methanol-ether azeotrope overhead which is water-washed to give pure ether raffinate plus ether-methanol bottoms, the latter being azeotropically distilled to yield ether-methanol overhead which is recycled to water washing.

The preparation of methyl tert-butyl ether from methyl and tert-butyl alcohols is discussed in S. V. Rozhkov et al., Prevrashch Uglevodorodov, Kislotno-Osnovn. Geterogennykh Katal. Tezisy Dokl. Vses Konf., 1977, 150 (C. A. 92:58165y). Here the TBA and methanol undergo etherification over KU-2 strongly acidic sulfopolystyrene cation-exchangers under mild conditions. This reference contains data on basic parameters of such a process. It is also pointed out that, although a plant for etherification over cation exchangers does not present any major problems, considerations include the fact that recycling large amounts of tert-butyl alcohol and methanol, as well as isobutylene, causes the scheme to be somewhat more expensive. Also, the progress of the reaction over cation exchangers is usually complicated by various adsorption and diffusion factors, by swelling phenomena, and by the variable distribution of the components between the solution and ion-exchanger phase. These ion-exchange resins may also be sensitive to small concentrations of peroxides in the feed. The peroxides may cause cross-linking and loss of activity. Furthermore, said acidic cation-exchangers with an organic (polystyrene or polymethacrylate) backbone generally have a very limited stability range with regard to operating temperatures, with temperatures above 120° C. normally leading to irreversible destruction of the resin and loss of catalytic activity.

In U.S. Pat. No. 2,282,469 to Frolich there is disclosed a process for preparing methyl tertiary butyl ether over a catalyst comprising Kieselguhr impregnated with phosphoric acid at a temperature of about 175° F. to 350° F.

Japanese Patent 0007432 teaches the use of zeolites to make dialkyl ethers containing primary or secondary alkyl groups. The zeolites have a porous structure and are represented by:

$$M_{2/n}O \cdot Al_2O_3 \cdot xSiO_2 \cdot yH_2O$$

where M is an alkali metal or alkaline earth metal cation or organic base cation, n is the valence of the cation and x and y are variables.

U. S. Pat. No. 4,058,576 to Chang et al. teaches the use of (pentasil-type) aluminosilicate zeolites, such as ZSM-5, having a pore size greater than 5 angstrom units and a silica-to-alumina ratio of at least 12, to convert lower alcohols to a mixture of ethers and olefins.

In U.S. Pat. No. 4,822,921 there is disclosed a method for producing MTBE by reacting tertiary butyl alcohol and methanol in the presence of a catalyst comprising an inert support, such as titania, having a phosphoric acid impregnated thereon.

U.S. Pat. No. 4,827,048 discloses a method for producing MTBE by reacting tertiary butyl alcohol and methanol in the presence of a catalyst comprising a heteropoly acid such as 12-tungstophosphoric acid or 12-molybdophosphoric acid on an inert support, such as titania.

Sanderson U.S. Pat. No. 4,900,850 discloses a method for removing ditertiary butyl peroxide from t-butyl alcohol by water extraction.

Sanderson et al. also disclose catalytic methods for the purification of t-butyl alcohol contaminated with residual quantities of tertiary butyl hydroperoxide and ditertiary butyl peroxide using catalysts such as catalysts composed of mixtures of nickel, copper, chromia and iron (U.S. Pat. No. 4,704,482), catalysts composed of mixtures of iron, copper, chromia and cobalt (U.S. Pat. No. 4,705,903), catalysts composed of mixtures of nickel, copper, chromium and barium (U.S. Pat. No. 4,873,380), or catalysts composed of metals selected from group VIB or VIIIB of the Periodic Table (U.S. Pat. No. 4,742,179).

It has heretofore been proposed, as shown, for example, by Grane U.S. Pat. No. 3,474,151 to thermally decompose tertiary butyl hydroperoxide and ditertiary butyl peroxide to form tertiary butyl alcohol. The thermal decomposition must be conducted with care, as pointed out by Grane, in that tertiary butyl alcohol will start to dehydrate at a temperature of about 450° F. and in that the dehydration becomes rapid at temperatures above about 475° F. Moreover, the product from the thermal decomposition normally contains a minor amount of tertiary butyl hydroperoxide and ditertiary butyl peroxide which have an adverse effect upon the quality of motor fuels and must be substantially completely removed if the tertiary butyl alcohol is to be fully effective. Grane proposes to accomplish this thermally by heating tertiary butyl alcohol containing small quantities of such peroxides at a temperature of 375°–475° F. for a period of 1 to 10 minutes.

This concept was expanded upon by Grane et al. in U.S. Pat. Nos. 4,294,999 and 4,296,262 to provide integrated processes wherein, starting with isobutane, motor-fuel grade tertiary butyl alcohol was prepared by the oxidation of isobutane (e.g., in the presence of a solubilized molybdenum catalyst) to produce a mixture of tertiary butyl alcohol and tertiary butyl hydroperoxide from which a fraction rich in tertiary butyl hydroperoxide could be recovered by distillation. This stream, after being debutanized was subjected to thermal decomposition under pressure at a temperature of less than 300° F. for several hours to significantly reduce the concentration of the tertiary butyl hydroperoxide. However, the product of this thermal decomposition step still contained residual tertiary butyl hydroperoxide, most of which was thereafter removed by a final thermal treatment of the contaminated tertiary butyl hydroperoxide in the manner taught by Grane U.S. Pat. No. 3,474,151.

Thus, the removal of trace quantities of tertiary butyl hydroperoxide from motor grade tertiary butyl alcohol has received appreciable attention. However, little appears to have been published concerning the removal of trace quantities of ditertiary butyl peroxide, the more refractory of the two peroxides. This may be explainable both because ditertiary butyl peroxide is not always present in trace quantities in motor grade tertiary butyl alcohol (its presence or absence being a function of the reaction conditions used in oxidizing the isobutane starting material) and because, when present, it is present in significantly lower amounts. For example, after decomposition of the major amount of tertiary butyl hydroperoxide formed by the oxidation of isobutane, the tertiary butyl hydroperoxide residual content will normally be about 0.1 to about 1 wt. %, based on the tertiary butyl alcohol, while the residual ditertiary butyl peroxide content, if any, will only be about 0.1 to 0.5 wt. %.

It has also been proposed to remove the residual hydroperoxide contaminants from tertiary butyl alcohol through the use of a heterogeneous cobalt oxide catalyst containing a copper oxide promoter as shown, for example, by Coile U.S. Pat. No. 4,059,598. Allison et al. in U.S. Pat. No. 3,505,360 have more generically taught that alkenyl hydroperoxides can be decomposed catalytically through the use of a catalyst based on a metal or compound of a metal of group IV-A, V-A or VI-A.

In West German DE 3248465-A a two-step process is disclosed wherein isobutane is oxidized noncatalytically with air to a conversion of about 48–90% to form the corresponding hydroperoxide, which is then catalytically decomposed under hydrogenation conditions in the presence of a supported catalyst such as palladium, platinum, copper, rhenium, ruthenium or nickel to form tertiary butyl alcohol. The decomposition product obtained using 1.3 % palladium on lithium spinel as a catalyst contained significant quantities of acetone, water and methanol.

BACKGROUND

When isobutane is reacted with molecular oxygen the principal products of the reaction are tertiary butyl alcohol and tertiary butyl hydroperoxide. However, minor amounts of other peroxides, including ditertiary butyl peroxide are also formed. Generally speaking, from about 10 to about 100 parts of tertiary butyl hydroperoxide are formed per part of ditertiary butyl peroxide. Minor quantities of other contaminants are also formed.

A listing of the components present in a representative reaction product, and their nominal boiling points is given in Table A.

TABLE A

| Component | NBP (°C.) |
| --- | --- |
| Isobutane | −11.7 |
| Methyl formate | 31.8 |
| Acetone | 56.3 |
| Isobutylene oxide | 60.0 |
| Isobutyraldehyde | 64.1 |
| Methanol | 64.7 |
| Methyl-t-butyl peroxide | 74.2 |
| Isopropyl alcohol | 82.3 |

TABLE A-continued

| Component | NBP (°C.) |
|---|---|
| Tertiary butyl alcohol | 82.4 |
| Ditertiary butyl peroxide | 111.0 |
| t-butyl-i-pr-peroxide | 124.0 |
| Tertiary butyl formate | 163.8 |
| Allyl tertiary butyl peroxide | |

The minor by-products are difficult to remove. For example, tertiary butyl formate (TBF) has a higher boiling point than ditertiary butyl hydroperoxide but tends to distill overhead, which suggests that it forms a minimum boiling azeotrope with another component or components.

When tertiary butyl alcohol is prepared by the catalytic decomposition of tertiary butyl hydroperoxide or by the catalytic reaction of tertiary butyl hydroperoxide with an olefin such as propylene, the tertiary butyl alcohol will be contaminated with residual quantities of tertiary butyl hydroperoxide, ditertiary butyl peroxide and allyl tertiary butyl peroxide, as explained above, and if tertiary butyl alcohol prepared in this manner is used as a feedstock for the direct preparation of MTBE by reaction with methanol, the tertiary butyl hydroperoxide and ditertiary butyl peroxide impurities will remain with the MTBE, and must be removed to the lowest level that is feasibly possible if the MTBE is to be used in the preparation of fuel for internal combustion engines.

Normally, the reaction between the tertiary butyl alcohol and the methanol will be a catalytic reaction, as explained above, in order to optimize the production of methyl tertiary butyl ether. It is customary practice to use a molar excess of methanol so that the consumption of tertiary butyl alcohol will be optimized. Even so, however, conversion of the tertiary butyl alcohol is normally incomplete and the conversion product will normally comprise methyl tertiary butyl ether, unreacted methanol, unreacted tertiary butyl alcohol and impurities, including peroxide impurities, introduced into the process through the use of a tertiary butyl alcohol feedstock prepared by the oxidation of isobutane. When the methyl tertiary butyl ether is recovered from the conversion product, typically by distillation, a distillation fraction is recovered that contains only a minor amount of methyl tertiary butyl ether and which comprises the unreacted methanol, unreacted tertiary butyl alcohol and impurities, including peroxide impurities. If this distillation fraction is to be recycled, the peroxide impurities must be removed to prevent their build-up in the system.

SUMMARY OF THE INVENTION

Catalytic or thermal decomposition of tertiary butyl hydroperoxide and ditertiary butyl peroxide can result in the formation of acetone and other low value by-products. Thus, the favorable effect that is obtained by the substantially complete elimination of the two peroxides will be to some extent counterbalanced if the decomposition product produces significant quantities of acetone.

It has been discovered in accordance with the present invention that a recycle stream from an MTBE reactor that consists mainly of TBA and methanol and that is contaminated with residual amounts of tertiary butyl hydroperoxide, ditertiary peroxide and allyl tertiary butyl peroxide can be both enriched and purified through the substantially complete removal of peroxide contaminants by bringing the contaminated recycle stream into contact with a silica-supported nickel, copper, iron and chromium catalyst, as defined hereafter, at a superatmospheric pressure at a temperature of about 80° to about 220° C., and more preferably at a temperature of about 100° to about 180° C. The best results are obtained at a temperature of about 160° to about 180° C.

Quite unexpected and surprising is our discovery that one of the more significant reaction products that is formed by the treatment of a peroxide-contaminated recycle stream is methyl tertiary butyl ether. Thus, both the quality and quantity of the methyl tertiary butyl ether reaction product are enhanced through the provision of the process of the present invention.

Removal of the peroxides from the recycle stream will increase the life of ion-exchange resins used for the production of MTBE.

STARTING MATERIALS

The starting materials for the process of the present invention include a recycle stream from an MTBE reactor. The recycle stream consists mainly of TBA and methanol and is contaminated with tertiary butyl hydroperoxide and ditertiary butyl peroxide.

Normally, the recycle stream will comprise about 40 to 60 wt. % of methanol and, correspondingly, about 50 to 25 wt. % of tertiary butyl alcohol, the remaining 5 to 15 wt. % of the recycle stream comprising unrecovered methyl tertiary butyl ether, peroxide contaminants, isobutylene and oxygenated impurities such as acetone.

The levels of contamination of such materials are such that the recycle stream will normally contain, prior to treatment, from about 0.05 to about 5 wt. % of tertiary butyl hydroperoxide and from about 0.05 to about 5 wt. % of ditertiary butyl peroxide.

Catalytic Treatment of MTBE Recycle Stream

In accordance with the present invention, an MTBE recycle stream, as above described, is brought into contact with a catalyst of the present invention under reaction conditions correlated to catalytically convert the peroxide contaminants, such as tertiary butyl hydroperoxide, ditertiary butyl peroxide and allyl tertiary butyl peroxide contaminants in the recycle stream to products including MTBE and isobutylene with not more than a minor increase in the concentration of acetone and other low value by-products.

The reaction may be conducted batchwise in an autoclave using powdered catalyst or may be conducted on a continuous basis by passing the recycle stream through a reactor containing a bed of a catalyst of the present invention under reaction conditions including a temperature within the range of about 80° to about 180° C. The reaction is suitably conducted at 0 to 10,000 psig., and more preferably at 200 to 1,000 psig. When the reaction is conducted batchwise, contact time may suitably be from about 0.5 to about 4 hours. When the reaction is conducted on a continuous basis, the recycle stream should be passed over the bed of catalyst at a liquid hourly space velocity of about 0.25 to about 5 pounds of liquid feed per hour per pound of catalyst.

The Nickel, Copper, Chromia, Iron Catalyst

The catalyst to be used in accordance with the present invention is a silica-supported catalyst that consists essentially of the metals and/or oxides of nickel, copper, chromium and iron in the proportions (on an oxygen-free basis) of about 1 to about 20 wt. % of iron, about 1 to about 6 wt.

% of chromium with the balance being nickel and copper in the weight ratio of about 2 to 3 parts of nickel per part of copper. For example, the catalyst compositions of the present invention may consist essentially of about 30 to 60 wt. % of nickel, about 5 to about 40 wt. % of copper, about 0.5 to about 10 wt. % of chromium and about 1 to about 30 wt. % of iron, with the nickel and copper being proportioned as indicated above.

More preferably, the catalyst compositions of the present invention will contain about 1 to about 20 wt. % of iron and about 1 to about 5 wt. % of chromium, with the nickel and copper being proportioned as indicated above. When the catalyst is prepared in the oxide form, it will tend to be reduced to the metallic form during use.

The nickel, copper, chromium and iron catalysts to be used in accordance with the present invention are supported on a suitable silica support such as Keiselguhr or silica-alumina, etc. The silica support may suitably comprise from about 20 to about 98 wt. % of the total weight of the catalyst composition and, more preferably from about 40 to about 95 wt. %.

Although the catalyst compositions of the present invention may be used in powdered form in conducting batch reactions, their utility is enhanced when they are used in pelleted form in a continuous reaction. When the catalyst is used in pelleted form in a continuous reaction, it is necessary that the pellets have good physical and chemical properties so that they will not disintegrate or break during the course of the continuous peroxide reduction. The pelleted catalyst compositions of the present invention have such properties.

Catalytic Treatment of MTBE Recycle Stream

In accordance with the present invention, a MTBE recycle stream consisting mainly of TBA and methanol contaminated with oxygenated impurities including tertiary butyl hydroperoxide, ditertiary butyl peroxide and allyl tertiary butyl peroxide is brought into contact with a catalyst of the present invention under reaction conditions correlated so as to substantially selectively convert the peroxide contaminants to tertiary butyl alcohol and methanol, with not more than a minor increase in the level of deleterious oxygenated by-products such as acetone. A significant quantity of MTBE is formed under the reaction conditions.

The reaction may be conducted batchwise in an autoclave using powdered catalyst or may be conducted on a continuous basis by continuously passing the contaminated recycle stream through a continuous reactor containing a bed of a catalyst of the present invention under reaction conditions including a temperature within the range of about 80° to about 220° C., and more preferably from about 100° to about 180° C. The reaction is suitably conducted at a pressure of about 0 to about 10,000 psig., and more preferably at a pressure of about 200 to about 1,000 psig. When the reaction is conducted batchwise, contact time may suitably be from about 0.5 to 4 hours. When the reaction is conducted on a continuous basis, the recycle stream should be passed through the bed of catalyst at a liquid hourly space velocity of about 0.25 to about 5 lbs. of feedstock per hour per pound of catalyst.

The specific correlation of reaction conditions to be utilized with any specific catalyst of the present invention can be determined by one of ordinary skill in the art with comparative ease. Thus, for example, the treated recycle stream can be analyzed after catalytic treatment to determine the level of contamination by peroxide by-products such as tertiary butyl hydroperoxide, ditertiary butyl peroxide and allyl tertiary butyl peroxide. If there is an insufficient reduction in peroxide contamination such that a significant amount (e.g., more than about 0.05 wt. %) of peroxide contaminants are still present, the severity of the reaction conditions should be increased in any suitable manner, such as by increasing one or more of the reaction temperature, the reaction pressure or the contact time. If, on the other hand, there is an undesirable increase in the level of other impurities such as acetone, the reaction conditions should be ameliorated by decreasing one or more of the reaction temperature or the contact time.

WORKING EXAMPLES

Reactor

The reactor was a stainless steel tube (1"×30") which was electrically heated. The catalyst bed was 250 cc. Liquid feed was pumped into the bottom of the reactor. Pressure regulation was with a Skinner Uni-Flow valve and a Foxboro controller. The liquid feed was pumped with a Ruska dual drive pump.

Feed

The "pseudo-recycle" feed for the decomposition reactor was 10% water, 45% methanol, 35% TBA, 5% MTBE, and 5% DTBP. We have found that if a catalyst is effective for the removal of DTBP, it will also be effective for the removal of the other peroxides such as TBHP, HTBP, etc., since DTBP is, by far, the most stable peroxide present.

TABLE 1

CATALYTIC DECOMPOSITION OF DTBP IN AN MTBE RECYCLE STREAM

| Notebook Number | 6773-1-F | 6773-3-1 | 6773-3-2 | 6773-3-3 | 6773-3-4 |
|---|---|---|---|---|---|
| Catalyst | | NiCuCrFe on Kgr | NiCuCrFe on Kgr | NiCuCrFe on Kgr | NiCuCrFe on Kgr |
| Reactor (cc) | | 250 | 250 | 250 | 250 |
| Pressure (psig) | | 500 | 500 | 500 | 500 |
| Feed Rate (cc/hr) | | 125 | 125 | 125 | 125 |
| Temperature (°C.) | | 120 | 140 | 160 | 180 |
| Time on Stream (hr) | | 5 | 5 | 5 | 5 |
| Space Vel. (cc/cc) | | 0.5 | 0.5 | 0.5 | 0.5 |
| DTBP Conv. (%) | | 78.9 | 98.0 | 99.9 | 99.9 |
| Remarks | $H_2O$ Free Basis | $H_2O$ Free Basis | $H_2O$ Free Basis | $H_2O$ Free Basis | $H_2O$ Free Basis |
| Composition | | | | | |
| IC4= | 0.005 | 0.031 | 0.233 | 1.642 | 1.922 |
| MEOH | 49.446 | 49.333 | 49.170 | 48.768 | 54.565 |

TABLE 1-continued

CATALYTIC DECOMPOSITION OF DTBP IN AN MTBE RECYCLE STREAM

| Notebook Number | 6773-1-F | 6773-3-1 | 6773-3-2 | 6773-3-3 | 6773-3-4 |
|---|---|---|---|---|---|
| Acetone | 0.019 | 0.466 | 0.816 | 1.147 | 1.362 |
| MTBE | 5.630 | 5.563 | 7.474 | 17.224 | 23.648 |
| TBA | 39.173 | 43.297 | 41.918 | 30.294 | 16.621 |
| DTBP | 5.632 | 1.190 | 0.115 | 0.003 | 0.004 |

TABLE 2

CATALYTIC DECOMPOSITION OF DTBP IN AN MTBE RECYCLE STREAM

| Notebook Number | 6773-1-F | 6773-2-1 | 6773-2-2 | 6773-2-3 | 6773-2-4 |
|---|---|---|---|---|---|
| Catalyst |  | NiCuCrFe on Kgr | NiCuCrFe on Kgr | NiCuCrFe on Kgr | NiCuCrFe on Kgr |
| Reactor (cc) |  | 250 | 250 | 250 | 250 |
| Pressure (psig) |  | 500 | 500 | 500 | 500 |
| Feed Rate (cc/hr) |  | 460 | 460 | 460 | 460 |
| Temperature (°C.) |  | 120 | 140 | 160 | 180 |
| Time on Stream (hr) |  | 5 | 5 | 5 | 5 |
| Space Vel. (cc/cc) |  | 1.8 | 1.8 | 1.8 | 1.8 |
| DTBP Conv. (%) |  | 26.26 | 52.56 | 90.27 | 99.61 |
| Remarks | $H_2O$ Free Basis | $H_2O$ Free Basis | $H_2O$ Free Basis | $H_2O$ Free Basis | $H_2O$ Free Basis |
| Composition |  |  |  |  |  |
| IC4= | 0.005 | 0.015 | 0.053 | 0.407 | 2.115 |
| MEOH | 49.446 | 49.338 | 49.344 | 48.982 | 48.935 |
| Acetone | 0.019 | 0.173 | 0.507 | 1.242 | 1.659 |
| MTBE | 5.630 | 5.629 | 5.826 | 8.328 | 14.959 |
| TBA | 39.173 | 40.593 | 41.475 | 39.806 | 30.970 |
| DTBP | 5.632 | 4.153 | 2.672 | 0.548 | 0.022 |

TABLE 3

CATALYTIC DECOMPOSITION OF DTBP IN AN MTBE RECYCLE STREAM

| Notebook Number | 6773-1-F | 6773-1-4 | 6773-1-1 | 6773-1-2 | 6773-1-3 |
|---|---|---|---|---|---|
| Catalyst |  | NiCuCrFe on Kgr | NiCuCrFe on Kgr | NiCuCrFe on Kgr | NiCuCrFe on Kgr |
| Reactor (cc) |  | 250 | 250 | 250 | 250 |
| Pressure (psig) |  | 500 | 500 | 500 | 500 |
| Feed Rate (cc/hr) |  | 300 | 300 | 300 | 300 |
| Temperature (°C.) |  | 120 | 140 | 160 | 180 |
| Time on Stream (hr) |  | 5 | 5 | 5 | 5 |
| Space Vel. (cc/cc) |  | 1.2 | 1.2 | 1.2 | 1.2 |
| DTBP Conv. (%) |  | 31.1 | 53.7 | 90.5 | 99.5 |
| Remarks | $H_2O$ Free Basis | $H_2O$ Free Basis | $H_2O$ Free Basis | $H_2O$ Free Basis | $H_2O$ Free Basis |
| Composition |  |  |  |  |  |
| IC4= | 0.005 | 0.017 | 0.037 | 0.454 | 2.529 |
| MEOH | 49.446 | 49.391 | 49.118 | 48.964 | 48.533 |
| Acetone | 0.019 | 0.199 | 0.340 | 1.121 | 1.636 |
| MTBE | 5.630 | 5.654 | 5.822 | 8.212 | 14.988 |
| TBA | 39.173 | 40.759 | 41.958 | 40.156 | 30.945 |
| DTBP | 5.632 | 3.882 | 2.610 | 0.535 | 0.027 |

The NiCuCrFe on Kgr catalyst used in the experiments contained about 30 wt. % of nickel, about 13 wt. % of copper, about 1 wt. % of chromium, about 3 wt. % of iron, and about 47 wt. % of silica support.

Note from Table 1, conducted at a comparatively slow feed rate of 125 cc/hr, that under the reaction conditions employed in this series of runs there was only an insignificant increase in the content of MTBE in the reaction product at a reaction temperature of 120° C., but that there was a striking decrease in DTBP content. The significant increase in acetone content indicates that the principle decomposition product in this run was acetone and that there was a modest formation of isobutylene and also a significant increase in the formation of TBA. At 140° C., conversion increased, as did the formation of MTBE. There was also an increased formation of isobutylene and acetone and a minor consumption of TBA.

However, when the reaction temperature was increased to 160° C., conversion approached 100%, substantially all of the DTBP was decomposed. Moreover, the formation of MTBE increased sharply and there was only a moderate increase in isobutylene and acetone formation.

At 180° C., conversion and decomposition of DTBP are again quantitative and there is also a dramatic increase in MTBE production, a net production of methanol, again, only a modest production of isobutylene and acetone and, also, a remarkable consumption of TBA.

A similar pattern is discernable from Table 2, conducted at a comparatively fast feed rate of 460 cc/hr. There was a low conversion and only a partial decomposition of the DTBP and no discernible increase in the content of MTBE in the reaction product at a reaction temperature of 120° C. and only a modest decrease in DTBP content. There was, again, an increase in acetone content and in isobutylene content and a slight increase in the formation of TBA. At 140° C., conversion increased, but there was no significant formation of MTBE. There was also an increased formation of isobutylene, acetone and TBA.

However, when the reaction temperature was increased to 160° C., conversion increased and substantially all of the DTBP was decomposed. Moreover, MTBE was formed and there was only a moderate increase in isobutylene formation and a much larger increase in acetone formation.

At 180° C., conversion and decomposition of DTBP are again quantitative and there is also a dramatic increase in MTBE production, a slight production of methanol, again, increased production of isobutylene and acetone and, also, a significant consumption of TBA.

In the runs reported in Table 3, an intermediate feed rate of 300 cc/hr was employed. There was a low conversion and only a partial decomposition of the DTBP and no discernible increase in the content of MTBE in the reaction product at a reaction temperature of 120° C. and only a modest decrease in DTBP content. There was, again, an increase in acetone content and in isobutylene content and a slight increase in the formation of TBA. At 140° C., conversion increased, but there was no significant formation of MTBE. There was also an increased formation of isobutylene, acetone and TBA.

However, when the reaction temperature was increased to 160° C., conversion increased and substantially all of the DTBP was decomposed. Moreover, MTBE was formed and there was only a moderate increase in isobutylene formation and a much larger increase in acetone formation.

At 180° C., conversion and decomposition of DTBP are again quantitative and there is also a dramatic increase in MTBE production, again, an increased production of isobutylene and acetone and, also, a significant consumption of TBA.

Example II

In our laboratories, the inventors herein and others have investigated the purification of tertiary butyl alcohol peroxide contaminated with contaminants including peroxide contaminants, isobutylene and methanol. Our investigation resulted in several inventions that have been patented, including:

Sanderson et al. U.S. Pat. No. 4,704,482
Sanderson et al. U.S. Pat. No. 4,705,903
Sanderson et al. U.S. Pat. No. 4,742,179
Sanderson et al. U.S. Pat. No. 4,873,380

The silica-supported catalyst used in Sanderson et al. U.S. Pat. No. 4,704,482 is the same catalyst that is used in accordance with the present invention. The experimental results reported in that patent, and the other patents of the group report the presence of acetone, methanol and isobutylene, but no mention is made of methyl tertiary butyl ether.

In our prior art patents, no mention was made of MTBE because none was found. Detection limits are about 0.001 wt. %.

However, since only a minor amount of methanol was normally present, this may account for the absence of MTBE in the products.

Having thus described our invention, what is claimed is:
1. A method for the catalytic decomposition of peroxides to purify a methyl tertiary butyl ether recycle stream consisting essentially of about 40 to about 60 wt. % of methanol, about 50 to 25 wt. % of tertiary butyl alcohol, about 5 to about 15 wt. % of methyl tertiary butyl ether, from about 0.5 to about 5 wt. % of tertiary butyl hydroperoxide and from about 0.05 to about 5 wt. % of ditertiary butyl peroxide which comprises the steps of:
   contacting said recycle stream in a reaction zone with a catalyst at a temperature of about 160° to about 180° C., a pressure of about 200 to 1000 psig and a flow rate of about 100 to about 500 cc of feed per hour per 250 cc of reactor volume sufficient to substantially completely decompose said peroxide contaminants and to form additional methyl tertiary butyl ether,
   said catalyst being a silica-supported catalyst consisting essentially of from about 40 to about 95 wt. % of silica and about 5 to about 60 wt. % of nickel, copper, chromium and iron, the metal components of the catalyst being proportioned, on an oxides-free basis, so as to contain about 30 to about 60 wt. % of nickel, about 5 to about 40 wt. % of copper, about 1 to about 5 wt. % of chromium and about 1 to about 20 wt. % of iron, with the nickel and copper being proportioned in the weight ratio of about 2 to 3 parts of nickel per part of copper.
2. A method as in claim 1 wherein the silica support is keiselguhr.

* * * * *